US00PP30884P3

(12) United States Plant Patent
Wain

(10) Patent No.: US PP30,884 P3
(45) Date of Patent: Sep. 17, 2019

(54) CHRYSANTHEMUM PLANT NAMED 'FICHRYMERCHEPU'

(50) Latin Name: *Chrysanthemum X morifolium*
Varietal Denomination: Fichrymerchepu

(71) Applicant: DUMMEN GROUP B.V., De Lier (NL)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,522

(22) Filed: Nov. 21, 2017

(65) Prior Publication Data

US 2018/0146593 P1 May 24, 2018

Related U.S. Application Data

(60) Provisional application No. 62/497,574, filed on Nov. 22, 2016.

(51) Int. Cl.
*A01H 5/02* (2018.01)
*A01H 6/14* (2018.01)

(52) U.S. Cl.
USPC ..... Plt./287
CPC ..... *A01H 6/1424* (2018.05); *A01H 5/02* (2013.01)

(58) Field of Classification Search
USPC ..... Plt./287, 292, 293
CPC ..... A01H 5/0255; A01H 5/02; A01H 5/00; A01H 6/1424; A01H 6/14
See application file for complete search history.

(56) References Cited

PUBLICATIONS

BFG Raker 2017 Mum, Aster, and Montauk Daisy Program, retrieved on Oct. 30, 2018, retrieved from the Internet at https://www.bfgsupply.com/_CE/pagecontent/Documents/Plant%20Connection/2017%20Raker%20Garden%20Mum%20Product%20List.pdf, 7 pp. (Year: 2017).*
SHS Griffin New Garden Mum Varieties Hot new introductions for 2016, retrieved on Oct. 29, 2018, retrieved from the Internet at http://www.griffins.com/pdf/email/2015/shs/New%20Garden%20Mum%20Varieties.pdf, pp. 1-26. (Year: 2016).*
Raker 2017 Mum Aster Daisy, retrieved on Oct. 30, 2018, retrieved from the Internet at www.raker.com/doc/2017. raker.mum.aster. daisy.pdf, 6 pp. (Year: 2017).*

* cited by examiner

*Primary Examiner* — June Hwu
(74) *Attorney, Agent, or Firm* — C. A. Whealy

(57) ABSTRACT

A new and distinct cultivar of *Chrysanthemum* plant named 'Fichrymerchepu', characterized by its upright to outwardly spreading and uniformly and broadly mounded plant habit; moderately vigorous growth habit; freely branching habit; dense and full plant form; uniform and freely flowering habit; medium-sized decorative-type inflorescences with dark red purple-colored ray florets; mid-season flowering habit, grown under natural season conditions, plants begin flowering in early to mid-September in the United Kingdom; and good garden performance.

1 Drawing Sheet

Botanical designation: *Chrysanthemum* X *morifolium*.
Cultivar denomination: 'FICHRYMERCHEPU'.

BACKGROUND OF THE INVENTION

The present invention relates to a new and distinct *Chrysanthemum* plant, botanically known as *Chrysanthemum* X *morifolium*, commercially grown as a garden *Chrysanthemum* plant, referred to as code number 65772 in U.S. Provisional Patent Application Ser. No. 62/497,474 and hereinafter referred to by the name 'Fichrymerchepu'.

The new *Chrysanthemum* plant is a product of a planned breeding program conducted by the Inventor in Fareham, Hampshire, United Kingdom. The objective of the breeding program is to create new mid-season flowering garden *Chrysanthemum* plants with numerous attractive inflorescences.

The new *Chrysanthemum* plant originated from a cross-pollination made in January, 2009 by the Inventor in Fareham, Hampshire, United Kingdom of an unidentified selection of *Chrysanthemum* X *morifolium*, not patented, as the female, or seed, parent with an unidentified selection of

*Chrysanthemum* X *morifolium*, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2009.

Asexual reproduction of the new *Chrysanthemum* plant by terminal vegetative cuttings was first conducted in Fareham, Hampshire, United Kingdom in December, 2009. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fichrymerchepu'. These characteristics in combination distinguish 'Fichrymerchepu' as a new and distinct *Chrysanthemum* plant:

1. Upright to outwardly spreading and uniformly and broadly mounded plant habit.
2. Moderately vigorous growth habit.
3. Freely branching habit; dense and full plant form.
4. Uniform and freely flowering habit.
5. Medium-sized decorative-type inflorescences with dark red purple-colored ray florets.
6. Mid-season flowering habit, grown under natural season conditions, plants begin flowering in early to mid-September in the United Kingdom.
7. Good garden performance.

Plants of the new *Chrysanthemum* can be compared to plants of the female and male parent selections. Plants of the new *Chrysanthemum* differ primarily from plants of the parent selections in time to flower as plants of the new *Chrysanthemum* flower earlier than plants of the parent selections.

Plants of the new *Chrysanthemum* can be compared to plants of *Chrysanthemum* X *morifolium* 'Fichryevenpur', disclosed in U.S. Plant patent application Ser. No. 15/732,504. In side-by-side comparisons, plants of the new *Chrysanthemum* differ primarily from plants of 'Fichryevenpur' in time to flower as plants of the new *Chrysanthemum* flower earlier than plants of 'Fichryevenpur'. In addition, plants of the new *Chrysanthemum* have slightly larger inflorescences than plants of 'Fichryevenpur'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant. The photograph is a top perspective view of a typical flowering plant of 'Fichrymerchepu' grown in a 14-cm container.

DETAILED BOTANICAL DESCRIPTION

The aforementioned photograph and following observations and measurements describe plants grown during the winter in 14-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were grown under long day/short night conditions for about five weeks (including propagation period) and then grown under short day/long night conditions to induce inflorescence initiation and development. Plants were twelve weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum* X *morifolium* 'Fichrymerchepu'.

Parentage:

*Female, or seed, parent.*—Unidentified selection of *Chrysanthemum* X *morifolium*, not patented.

*Male, or pollen, parent.*—Unidentified selection of *Chrysanthemum* X *morifolium*, not patented.

Propagation:

*Type.*—Terminal vegetative cuttings.

*Time to initiate roots, summer.*—About ten days at temperatures about 21° C.

*Time to initiate roots, winter.*—About twelve days at temperatures about 21° C.

*Time to produce a rooted young plant, summer.*—About three weeks at temperatures about 21° C.

*Time to produce a rooted young plant, winter.*—About four weeks at temperatures about 21° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous decorative-type garden *Chrysanthemum*; stems upright to outwardly spreading giving a uniformly and broadly mounded appearance to the plant; numerous lateral branches and relatively short internodes, dense and full plant form; moderately vigorous growth habit.

*Plant height.*—About 20 cm.

*Plant width.*—About 34 cm.

*Branching habit.*—Freely branching habit; about 17 lateral branches develop after removal of terminal apex (pinching).

*Lateral branches.*—Length: About 18 cm. Diameter: About 3 mm. Internode length: About 1 cm. Strength: Strong. Aspect: About 45° from vertical and then bending upwardly. Texture: Fine pubescence. Color: Close to 143C.

Leaf description:

*Arrangement.*—Alternate, simple.

*Length.*—About 4 cm.

*Width.*—About 3.2 cm.

*Shape.*—Palmately-lobed; roughly ovate with three to five lobes.

*Apex.*—Broadly acuminate.

*Base.*—Attenuate.

*Margin.*—Slightly dentate and palmately lobed; sinuses between lateral lobes mostly divergent.

*Texture, upper and lower surfaces.*—Fine pubescence; slightly rough; veins prominent on lower surface.

*Color.*—Developing leaves, upper surface: Close to 137A. Developing leaves, lower surface: Close to 137C. Fully expanded leaves, upper surface: Close to 146A; venation, close to 146B. Fully expanded leaves, lower surface: Close to 139C; venation, close to 146B.

*Petioles.*—Length: About 1.5 cm. Diameter: About 2 mm. Texture, upper and lower surfaces: Fine pubescence; slightly rough. Color, upper and lower surfaces: Close to 146B.

Inflorescence description:

*Form and flowering habit.*—Decorative-type inflorescence form with ligulate-shaped ray florets; inflorescences borne on terminals above and beyond the foliar plane; disc and ray florets arranged acropetally on a capitulum; freely flowering habit with about 221 inflorescences developing per plant during the flowering season.

*Fragrance.*—Strongly fragrant; pungent, herbaceous.

*Flowering response.*—Mid-season flowering habit, plants exposed to natural season conditions begin flowering in early to mid-September in the United Kingdom; plants flower uniformly and continuously during the flowering season.

*Inflorescence longevity.*—Inflorescences maintain good color and substance for about three to five weeks on the plant; inflorescences persistent.

*Inflorescence buds.*—Height: About 4 mm. Diameter: About 5 mm. Shape: Oblate. Color: Close to 137C.

*Inflorescence diameter.*—About 4 cm.

*Inflorescence height.*—About 1.5 cm.

*Receptacles.*—Height: About 2 mm. Diameter: About 3 mm. Shape: Conical. Color: Close to 145B.

*Ray florets.*—Number of ray florets per inflorescence: About 96 arranged in about eight whorls. Orientation: Initially upright, then about 70° from vertical. Length: About 1.4 cm. Width: About 6 mm. Shape: Ligulate. Apex: Emarginate. Base: Fused into a short tube. Margin: Entire. Texture, upper and lower surfaces: Smooth, glabrous; double-keeled. Color: When opening, upper surface: Close to 64A. When opening, lower surface: Close to 70B. Fully opened, upper surface: Close to 72A; with development, color becoming closer to 70A. Fully opened, lower surface: Close to N78C; color does not change with development.

*Disc florets.*—Disc floret initiation and development has not been observed on plants of the new *Chrysanthemum* to date.

*Phyllaries.*—Number of phyllaries per inflorescence: About 18 arranged in about three whorls. Length: About 6 mm. Width: About 2 mm. Shape: Lanceolate. Apex: Acute. Base: Obtuse. Margin: Entire. Texture, upper surface: Smooth, glabrous; waxy. Texture, lower surface: Fine pubescence; waxy. Color, upper surface: Close to 143A. Color, lower surface: Close to 137C.

*Peduncles.*—Length, terminal peduncle: About 3.9 cm. Diameter, terminal peduncle: About 2 mm. Angle: Erect to about 10° from vertical. Strength: Strong; flexible. Texture: Densely pubescent. Color: Close to 137D.

*Reproductive organs.*—Androecium: None observed. Gynoecium: Present only on ray florets. Pistil length: About 5 mm. Stigma shape: Bi-parted. Stigma color: Close to 9B. Style length: About 1 mm. Style color: Close to 1B. Ovary color: Close to NN155A.

*Seeds and fruits.*—Seed and fruit production has not been observed on plants of the new *Chrysanthemum* to date.

Disease & pest resistance: Resistance to pathogens and pests common to *Chrysanthemum* plants has not been observed on plants of the new *Chrysanthemum* to date.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fichrymerchepu' as illustrated and described.

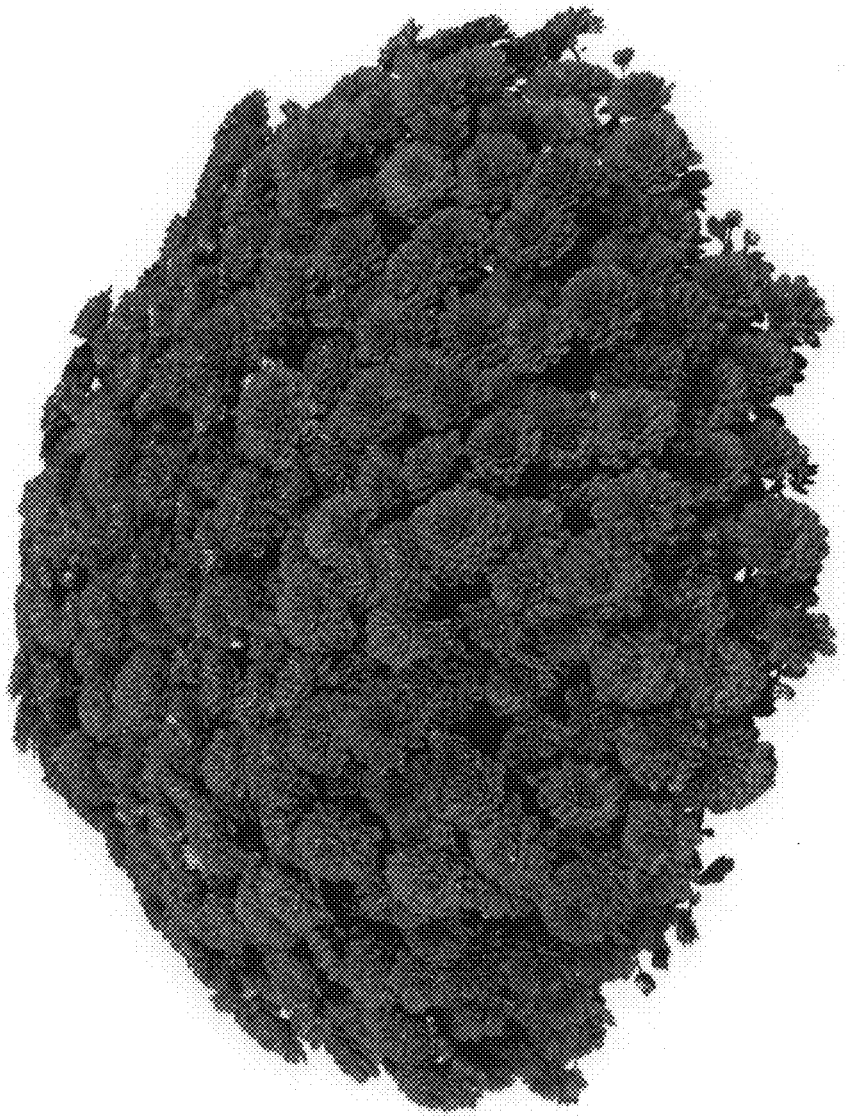

* * * * *